United States Patent [19]

Wilks et al.

[11] Patent Number: 5,972,922

[45] Date of Patent: *Oct. 26, 1999

[54] STEROIDS WHICH INHIBIT ANGIOGENESIS

[75] Inventors: John W. Wilks, Kalamazoo; Thomas F. DeKoning, Marcellus; Paul A. Aristoff, Kalamazoo, all of Mich.

[73] Assignee: Alcon Laboratories, Inc., Fort Worth, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/575,844

[22] Filed: Dec. 21, 1995

Related U.S. Application Data

[63] Continuation of application No. 08/308,061, Sep. 16, 1994, abandoned, which is a continuation of application No. 08/178,172, Jan. 6, 1994, abandoned, which is a continuation of application No. PCT/US91/03459, May 23, 1991, which is a continuation-in-part of application No. 07/609,661, Nov. 6, 1990, abandoned, which is a continuation-in-part of application No. 07/536,894, Jun. 11, 1990, abandoned.

[51] Int. Cl.[6] ............... C07J 31/00; C07J 9/00; C07J 51/00; A61K 31/56

[52] U.S. Cl. .......... 514/178; 514/171; 514/177; 514/179; 514/181; 552/507; 552/548; 552/553; 552/594; 552/608; 552/610

[58] Field of Search .................. 514/171, 177, 514/178, 181, 179; 552/548, 553, 594, 507, 610, 608

[56] References Cited

U.S. PATENT DOCUMENTS

| | | | |
|---|---|---|---|
| 3,067,193 | 12/1962 | Tishler et al. | 540/5 |
| 3,067,194 | 12/1962 | Tishler et al. | 540/9 |
| 3,158,601 | 11/1964 | Buchschacher et al. | 540/53 |
| 3,291,815 | 12/1966 | Pinson, Jr. | 552/573 |
| 3,300,483 | 1/1967 | Tishler et al. | 540/5 |
| 3,980,778 | 9/1976 | Ayer et al. | 424/243 |
| 4,018,918 | 4/1977 | Ayer et al. | 424/240 |
| 4,041,055 | 8/1977 | Shephard et al. | 260/397.3 |
| 4,599,331 | 7/1986 | Schreiber et al. | 514/179 |
| 4,704,358 | 11/1987 | Kominek et al. | 435/61 |
| 4,771,042 | 9/1988 | Braughler et al. | 514/171 |
| 4,975,537 | 12/1990 | Aristoff et al. | 540/9 |
| 5,001,116 | 3/1991 | Folkman et al. | 514/56 |

FOREIGN PATENT DOCUMENTS

| | | |
|---|---|---|
| 1188616 | 6/1985 | Canada ............... 514/171 |
| 0 123 241 | 10/1984 | European Pat. Off. . |
| 0 156 643 | 10/1985 | European Pat. Off. . |
| 0 186 948 | 7/1986 | European Pat. Off. . |
| 0 221 705 | 5/1987 | European Pat. Off. . |
| 0 268 400 | 5/1988 | European Pat. Off. . |
| 1938218 | 8/1972 | Germany . |
| 26 49 753 A1 | 5/1977 | Germany . |
| 631 999 | 10/1986 | Switzerland . |
| WO 86/00907 | 2/1986 | WIPO . |
| WO 87/01706 | 3/1987 | WIPO . |
| WO 87/02672 | 5/1987 | WIPO . |
| WO 90/15816 | 12/1990 | WIPO . |

OTHER PUBLICATIONS

Steroid Drugs, 1962, McGraw–Hill Book Company Inc. p. 3.
Science 221:719 (1983).
Folkman, et al., Annals of Surgery 206:374–383 (1987).
Coffey, R.J., J. Cell Physiol. 132:143–148 (1987).
J. National Cancer Institute, 81:1346–1351 (1989).
Gross, et al., Proc. National Academy of Sciences USA, 78:1176–1180 (1981).
Oikawa, et al., Cancer Letters, 43:85–92 (1988).
Ziche, et al., International Journal of Cancer, 35:549–552 (1985).
Penhallgon, et al., J. National Cencer Institute, 74:869–873 (1985).
Lee, Cancer Research, 47:5021–5024 (1987).
Teale, et al., European Journal of Cancer and Clinical Oncology 23:93–100 (1987).
J. Org. Chem., 33:1700 (1968).
Kano, et al., J. Org. Chem., 44(9):1582–1584 (1970).
Jacobsen, et al., J. Med. Chem., 33:1145–1151 (1990).
Van Rheenen et al. J.O.C., 44(9), 1582–4, 1979.
Drayer et al. Steroids, 44(4), 293–300, 1984.

*Primary Examiner*—Mukund J. Shah
*Assistant Examiner*—Brenda Coleman
*Attorney, Agent, or Firm*—Sally Yeager

[57] ABSTRACT

Novel angiostatic $\Delta^{4,9(11)}$-steroids (I),

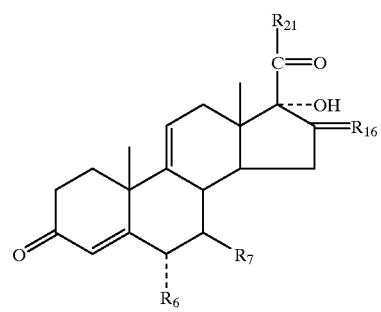

(I)

$C_{21}$-oxygenated steroids (II) and other known steroidal compounds have been found to be useful in treating angiogenesis in mammals who have a need for the same. These steroids are useful in treating diseases of neovascularization such as cancer, diabetes and arthritis.

11 Claims, No Drawings

STEROIDS WHICH INHIBIT ANGIOGENESIS

CROSS-REFERENCE TO RELATED APPLICATIONS

This application is a continuation-in-part, continuation, division, of application Ser. No. 08/308,061 filed Sep. 16, 1994, now abandoned which is a continuation of Ser. No. 08/178,172 filed Jan. 6, 1994, (abandoned), which is a continuation of PCT/US91/03459 filed May 23, 1991, which is a continuation-in-part of Ser. No. 07/609,661 filed Nov. 6, 1990, (abandoned), which is a continuation-in-part of Ser. No. 07/536,894 filed Jun. 11, 1990, (abandoned).

BACKGROUND OF THE INVENTION

1. Field of the Invention

The present invention includes novel compounds and a method of treating angiogenesis in mammals who have a need for the same which utilizes certain angiostatic $\Delta^{4,9(11)}$-steroids. These steroids are useful in treating diseases of neovascularization such as cancer, diabetes and arthritis.

2. Description of the Related Art

Angiogenesis is the development of blood vessels which typically would lead to a vascular bed capable of sustaining viable tissue. Angiogenesis is a necessary process in the establishment of embryonic tissue and development of a viable embryo. Similarly, angiogenesis is a necessary step in the establishment and development of tumor tissue as well as certain inflammatory conditions. The inhibition of angiogenesis would be useful in the control of embryogenesis, inflammatory conditions, and tumor growth, as well as numerous other conditions.

European patent application No 83870132.4 (Publication No 0 114 589) published Aug. 1, 1984 describes the use of cortisone, hydrocortisone and 11α-hydrocortisone in combination with heparin in the inhibition of angiogenesis.

The angiogensis inhibitory effects of heparin and heparin fragments in combination with cortisone is described in Science 221, 719 (1983). The use of heparin and heparin fragments in combination with hydrocortisone is set forth in the Proceedings of AACR 26, 384 (1985).

Heparin is presently used with inhibitors of angiogenesis, especially angiostatic steroids to treat diseases involving neovascularization, see Biochem. Pharmacol. 34, 905 (1985) and Annals of Surgery 206, 374 (1987). The heparin potentiates the angiogenesis-inhibiting activity of other drugs, for example of collagen biosynthesis inhibitors such as L-azetidine carboxylic acid. The problem with using heparin is that the efficacy of each preparation/batch of heparin differs due to the chemical heterogeneity of the heparin molecules.

Suramin inhibits the binding of fibroblast growth factor to its receptor during in vitro experiments. Fibroblast growth factor is one of a number of known angiogenic growth factors. See, J. Cell Physiol. 132, 143 (1987).

Suramin and 4,4'-bis[ [4-(o-hydroxyanilino)-6-(m-sulfoanilino)-s-triazin-2-yl]amino]-2,2'stilbenedisulfonic acid have been reported to possess antitumor activity. See, Gann 61, 569 (1970) and J. Clin. Oncol., 7, 499 (1989).

U.S. Pat. No. 4,599,331 discloses 20-substituted $\Delta^{1,4}$-16-methyl steroids which did not have a $\Delta^{9(11)}$ double bond which are useful as antiangiogenics when combined with heparin.

U.S. Pat. No. 4,771,042 discloses 21-hydroxy steroids which are useful in the inhibition of angiogenesis involving the co-administration of steroids with heparin or heparin fragments. The compounds of the present invention do not include —$CH_2$— at $C_{21}$.

International Patent Publication WO87/02672 discloses various $C_{11}$-functionalized steroids useful in the inhibition of angiogenesis when combined with heparin.

The Journal of the National Cancer Institute 81, 1346 (1989) discloses that "Suramin also appears to have antiangiogenesis activity . . . ".

The combination of suramin-type compounds and angiostatic steroids have been reported to treat angiogenesis in a warm blooded mammal, see the Journal of the National Cancer Institute 81, 1346 (1989) and U.S. patent application Ser. No. 07/483,044.

It is known that steroids alone can inhibit angiogenesis, see National Academy of Sciences USA 78, 1176 (1981) [medroxyprogesterone], Cancer Letters 43, 85 (1988) [medroxyprogesterone acetate], International Journal of cancer 35, 549 (1985) [cortisone], JNCI 74, 869 (1985) [cortisone], Cancer Research 47, 5021 (1987) [cortisone acetate] and European Journal of Cancer and Clinical Oncology 23, 93 (1987) [cortisone acetate]. The data reported in these publications is consistent with the clinicla practice of using steroids to inhibit tumors.

The angiostatic $\Delta^{4,9(11)}$-steroids (I), $C_{21}$-oxygenated steroids (II) as well as the individual compounds claimed of the present invention are usefull in treating diseases of neovascularization such as cancer, diabetes and arthritis without heparin, suramin or any other "potientator" and a method of inhibiting hair growth.

With regard to the $\Delta^{4,9(11)}$-steroids (I), in particular the compound of EXAMPLE 10 [21-bromo-6α-fluoro-17α-hydroxy-16α-methylpregna-4,9(11)-diene-3,20-dione], Swiss patent 631,999 discloses a 21-chloro-16β-methyl steroid and DE 1,938,218 discloses a 21-chloro-16α-methyl steroid without a 17α-hydroxy group.

The $C_{21}$-oxygenated steroids of formula (II) are known. More specifically, the the compound of EXAMPLE 2 is known, see U.S. Pat. No. 3,291,815; the compound of EXAMPLE 3 is known, see U.S. Pat. No. 4,771,042; the compound of EXAMPLE 4 is known, see U.S. Pat. Nos. 3,980,778 (column 2, compound 3) and 4,018,918 (column 10, compound 17); the compound of EXAMPLE 6 is known, see CAS 378-61-0. The compound of EXAMPLE 7 is known, see PCT/DE85/00249 Example 1 and U.S. Pat. No. 4,975,537 where the compound is generically claimed.

The compound of EXAMPLE 14 is known, see U.S. Pat. Nos. 4,771,042 and 4,704,358. The compound of EXAMPLE 13 is known, see J. Org. Chem., 33, 1700 1968. The compounds of EXAMPLES 2–4, 8, 11 and 12 are also known.

European Patent Publication 0 268 400 (examples 6 and 62), J. Org. chem., 44, 1582 (1970), J. Med. Chem., 33, 1145 (1990), Steroids, 44(4), 3243 (1984), European Patent Publication 0 123 241 and Offenlegungsschrift DT 26 49 753 A1 all disclose 21-bromo steroids similar to those of claim 1 where $R_{21}$ is —$CH_2$—Br.

International Publication No. WO87/01706 discloses various amino steroids but none have the same side chain identified as $R_{21}$, as the $\Delta^{4,9(11)}$-steroids (I) of the present invention.

17α,21-Dihydroxypregna4,9(11)-diene-3,20-dione is known, see U.S. Pat. Nos. 3,067,193, 3,067,194 (column 29, lines 43–44), 3,158,601 (column 24, lines 52–53), 3,300,483, EP 0 156 643 and EP 0 186 948.

6α-fluoro-17α-hydroxy-16β-methylpregna-4,9(11)-diene-3,20-dione 21-phosphate is known, see EP 0 221 705 (Example 13).

SUMMARY OF INVENTION

Disclosed is a $\Delta^{4,9(11)}$-steroid of formula (I) where $R_6$ is —H, —F or —$CH_3$;

$R_7$ is —H or —$CH_3$;

$R_{16}$ is α-$R_{16-1}$:β-$R_{16-2}$ where one of $R_{16-1}$ and $R_{16-2}$ is —H and the other of $R_{16-1}$ and $R_{16-2}$ is —H or —$CH_3$;

$R_{21}$, is —C(—$CH_2CH_2$—)—O—$R_{21-1}$, where $R_{21-1}$ is —H, —PO(OH)$_2$, or —CO—$R_{21-2}$ where $R_{21-2}$ is $C_1$–$C_{12}$ alkyl, —C($R_{21-3}$)($R_{21-4}$)—O—$R_{21-1}$ where $R_{21-3}$ is —H or $C_1$–$C_4$ alkyl, where $R_{21-4}$ is $C_1$–$C_4$ alkyl, and where $R_{21-1}$ is as defined above, —C($R_{21-2}$)($R_{21-3}$)—S—$R_{21-1}$ where $R_{21-1}$, $R_{21-3}$ and $R_{21-4}$ are as defined above, —$CH_2$—Br and pharmaceutically acceptable salts of the —PO(OH)$_2$.

Also disclosed is a method of treating angiogenesis in a warm blooded mammal who is in need of such treatment which comprises administration of an angiogenic inhibiting amount of a C21-oxygenated steroid of formula (II) where $R_6$ is —H, —F or —$CH_3$;

$R_7$ is —H or —$CH_3$;

$R_{16}$ is α-$R_{16-1}$:β-$R_{16-2}$ where one of $R_{16-1}$ and $R_{16-2}$ is —H and the other of $R_{16-1}$ and $R_{16-2}$ is —H or —$CH_3$;

$R_{21}$ is is —H, —PO(OH)$_2$, or —CO—$R_{21-1}$ where $R_{21-1}$ is $C_1$–$C_{12}$ alkyl.

Additionally disclosed is a method of treating angiogenesis in a warm blooded mammal who is in need of such treatment which comprises administration of an angiogenic inhibiting amount of the compounds of EXAMPLES 4, 8, 11–14.

Further disclosed are the compounds of EXAMPLES 1, 5 AND 9.

DETAILED DESCRIPTION OF THE INVENTION

The $\Delta^{4,9(11)}$-steroids (I), $C_{21}$-oxygenated steroids (II) and other steroids of the present invention can be readily prepared from steroids well known to those skilled in the art by methods known to those skilled in the art. For example, the 21-alkyl substituted $\Delta^{4,9(11)}$-steroids are prepared following the procedure of Yakugaku Zasshi 99, 380 (1979), Eur. Pat. Appl. 4,765 (Published 1979), Chem. Pharm. Bull., 23, 2728 (1975) and U.S. Pat. No. 3,280,159.

It is preferred that one of $R_{16-1}$ or $R_{16-2}$ is —$CH_3$. It is preferred that $R_{21}$ is —C(—$CH_2CH_2$—)—O—$R_{21-1}$ or —C($R_{21-3}$)($R_{21-4}$) —O—$R_{21-1}$. It is preferred that $R_{21-1}$ is —H or —CO—$CH_3$ and that $R_{21-3}$ and $R_{21-4}$ are not both —H. The notation —C(—$CH_2CH_2$—)—O—$R_{21-1}$ refers to a cyclopropyl group at $C_{21}$.

It is preferred that the $\Delta^{4,9(11)}$-steroids (I) is selected from the group consisting of 21-bromo-6α-fluoro-17α-hydroxy-16α-methylpregna-4,9(11)-diene-3,20-dione.

It is preferred that the $C_{21}$-oxygenated steroids (11) is selected from the group consisting of the compounds of EXAMPLES 2, 3 and 5–7; it is more preferred that the $C_{21}$-oxygenated steroids (II) is the compound of EXAMPLES 2 or 6; it is most preferred that the $C_{21}$-oxygenated steroids (II) is 6α-fluoro-17α,21-dihydroxy-16α-methylpregna-4,9(11)-diene-3,20-dione.

The 21-phosphates of the $\Delta^{4,9(11)}$-steroids are acids, and as such form base addition salts when reacted with bases of sufficient strength. The pharmaceutically acceptable salts include both inorganic and organic bases. The pharmaceutically acceptable salts are preferred over the free acids since they produce compounds which are more water soluble and more crystalline. The preferred pharmaceutically acceptable salts include salts of the following bases, for example, hydroxide, ammonia, tromethamine (THAM) and 2-amino-2-(hydroxymethyl)-1,3-propanediol. The $\Delta^{4,9(11)}$-steroids (I), C21-oxygenated steroids (II) and other steroids of the present invention are used in treating angiogenesis. It is preferred that the method of treating angiogenesis is the treatment of diseases of neovascularization. It is preferred that the indication for treatment is selected from the group consisting of solid tumors, diabetes, arthritis, atheroscl ersois, neovascularization of the eye, glaucoma, parasitic diseases, psoriasis, abnormal wound healing processes, hypertrophy following surgery, bums, injury, inhibition of hair growth, inhibition of ovulation and corpus luteum formation, ihibition of implantation and inhibition of embryo development in the uterus. It is more preferred that the neovascular disease is solid tumors, diabetes or arthritis.

The dose of the $\Delta^{4,9(11)}$-steroids (I), $C_{21}$-oxygenated steroids (II) and other steroids of the invention is from about 0.1 to about 100 mg/kg/day, preferably from about 0.1 to about 50 mg/kg/day.

For the inhibition of angiogenesis, the $\Delta^{4,9(11)}$-steroids (I), C21-oxygenated steroids (II) and other steroids of the invention may be combined with each other or with other agents such as suramin, sulfated glycosaminoglycans and sulfated polysaccharides, or effective fragments of these molecules. The preferred glycosaminoglycans include heparin and heparan sulfate. Fragments of heparin or heparan sulfate may also be used if they contain a minimum of six saccharide residues; fragments of heparin or heparan sulfate may be prepared from heparin or heparan sulfate isolated from natural sources, or they may be prepared by chemical synthesis. The $\Delta^{4,9(11)}$-steroids (I), $C_{21}$-oxygenated steroids (II) and other steroids of the invention may also be combined with polysaccharides including pentosan polysulphate, cyclodextrins, or other sulfated polysaccharides isolated from natural sources. The preferred polysaccharides are sulfated forms of β-cyclodextrin including β-cyclodextrin tetradecasulfate, pentosan polysulphate, or the polysaccharide-peptidoglycan isolated from Arthrobacter, Journal of Biochemistry 92, 1775 (1982). These polysaccharides may be isolated from natural sources, or prepared by chemical synthesis.

The $\Delta^{4,9(11)}$-steroids (I), $C_{21}$-oxygenated steroids (II) and other steroids of the invention may also be used in combination treatments containing compounds which interfere with collagen biosynthesis. Preferred compounds in this group include L-azetidine-2-carboxylic acid, thioproline, and related proline analogs. Also included are other inhibitors of basement membrane collagen synthesis such as 8,9-dihydroxy-7-methyl-benzo(b)quinolizinium bromide. The exact dosage and frequency of administration depends on the particular $\Delta^{4,9(11)}$-steroids (I), $C_{21}$-oxygenated steroids (II) and other steroids of the invention being used, the particular condition being treated, the severity of the condition being treated, the age, weight, general physical condition of the particular patient, other medication the individual may be taking as is well known to those skilled in the art and can be more accurately determined by measuring the blood level or concentration of the $\Delta^{4,9(11)}$-steroids (I), $C_{21}$-oxygenated steroids (II) and other steroids of the invention in the patient's blood and/or the patient's response to the particular condition being treated.

The $\Delta^{4,9(11)}$-steroids (I), $C_{21}$-oxygenated steroids (II) and other steroids of the invention of the present invention are also provide a method of inhibiting hair growth in mammals and more preferably in a human which comprises the topical administration of a composition comprising an angiostatic steroid of Formula (I) or (II). In practicing the present invention the $\Delta^{4,9(11)}$-steroids (I), $C_{21}$-oxygenated steroids (II) and other steroids of the invention are topically administered to an area on the body where hair growth is to be inhibited. The topical administration of the angiostatic steroid composition is typically done by routine applications to the hair follicles where hair growth is undesirable. The $\Delta^{4,9(11)}$-steroids (I), $C_{21}$-oxygenated steroids (II) and other steroids of the invention are present in an amount effective to have an anti-angiostatic result, preferably at least 1 mg/ml or from about 1 mg/ml to about 10 mg/ml. The dosage is, of course, dependent upon the circumstance of treatment and particular mammal treated which can be readily determined.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)$H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will he identified as being in the alpha ($\alpha$) configuration and is identified by a broken, dashed or dotted line attachment to the carbon atom, i.e., by the symbol "- - -" or ". . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —C($\alpha$-$R_{i-j}$)($\beta$-$R_{i-k}$)—. For example, when the bivalent variable $R_6$, —C(=$R_6$)— is defined to consist of two monovalent variable substituents, the two monovalent variable substituents are $\alpha$-$R_{6-1}$:$\beta$-$R_{6-2}$, . . . $\alpha$-$R_{6-9}$:$\beta$-$R_{6-10}$, etc, giving —C($\alpha$-$R_{6-1}$)($\beta$-$R_{6-2}$)—, . . . —C($\alpha$-$R_{6-9}$)($\beta$-$R_{6-10}$)—, etc. Likewise, for the bivalent variable $R_{11}$, —C(=$R_{11}$)—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . . " means a lactone in which the carbonyl is bonded to $C_2$. However, when designated ". . . $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention $(C_1$–$C_3)$alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and $(C_1$–$C_3)$alkoxy$(C_1$–$C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

φ refers to phenyl ($C_6H_5$).

MS refers to mass spectrometry expressed as m/e or mass/charge unit. [M+H]+ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

Treating refers to inhibiting and/or preventing.

Angiostatic steroids refer to those steroids which prevent the process of angiogenesis/neovascularization, or cause the regression of new vasculature which results from angiogenic stimuli.

Angiogenesis refers to neovascularization.

CAS refers to Chemical Abstracts Service (Columbus, Ohio) and NNNNNN—NN—N refers registry numbers where each "N" is an integer from 0 thru 9, hut deleting leading zeros in the 6-digit portion of the number. Registry numbers are assigned to a particular chemical compound by CAS criteria, provided that the compound has been found to exist and it has been characterized in some way. Compounds published from approximately 1967 to the present are registered publicly and the registry number is the key to finding references in the CAS data base for such a registered compound. The CAS data base is publicly available from several database vendors such as STN International, System Development Corporation (SDC) Orbit Search Service, Lockheed Dialog, Bibliographic Retrieval Systems, Questrel, etc. CAS registry numbers are included in the EXAMPLES for some of the compounds which have been registered.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1  6α-Fluoro-17α,21-dihydroxy-16α-methylpregna-4,9(11)-diene-3,20-dione Methanol (20 ml) and sodium methoxide (25%, 0.2 ml) is added to 6α-fluoro-17α,21-dihydroxy-16α-methylpregna-4,9(11)-diene-3,20-dione 21-acetate (U.S. Pat. No. 3,291,815, 1.0 g) in methanol. The reaction mixture is neutralized with acetic acid and concentrated to dryness under reduced pressure. The concentrate is distributed between water and chloroform. The organic layer is separated and washed twice with water and dried over anhydrous sodium sulfate. The crude solid is chromatographed over silica gel eluting with ethyl acetate/hexanc (35/65). The appropriate fractions are pooled and concentrated to give the title compound, mp 206–207°.

Example 1

17α,21-Dihydroxypregna-4,9(11)-diene-3,20-dione  17α,21-Dihydroxypregna-4,9(11)-diene-3,20-dione 21-acetate (U.S. Pat. No. 4,041,055, EXAMPLE 66, 500 g), potassium carbonate (15.0 g), methanol (2 l) and methylene chloride (1 l) are stirred at 20–25°. After 3 hr the solvents were slowly removed by reduced pressure for 45 min then heat is applied. Water (1 l) and acetic acid (25 ml) are added. The mixture is concentrated to 315 ml and the pot volume was below the original reaction volume. Water (1 l) is added and the mixture is permitted to stand overnight. The mixture is filtered and and washed with a small amount of water, dried under reduced pressure on the filter and then in a vacuum oven at 60° to give the title compound.

Example 2

6α-Fluoro-17α,21-dihydroxy-16α-methylpregna-4,9(11)-diene-3,20-dione 21-acetate (II)

See, U.S. Pat. No. 3,291,815.

Example 3

6α-Fluoro-17α,21-dihydroxy-16β-methylpregna-4,9(11)-diene-3,20-dione (II)

See, U.S. Pat. No. 4,771,042.

Example 4

6α-Fluoro-17α,21-dihydroxy-16β-methylpregna-4,9(11)-diene-3,20-dione 17,21-diacetate See, U.S. Pat. Nos. 3,980,778 (column 2, compound 3) and 4,018,918 (column 10, compound 17)

Example 5
6a-Fluoro-17α,21-dihydroxy-16β-methylpregna-4,9(11)-diene-3,20-dione 21-phosphate combined with 2-amino-2-(hydroxymethyl)-1,3-propanediol (1:2)

Acetonitrile (144 ml) and water (16 ml) is added to 6α-flouro-17,21-dihydroxy-16β-methylpregna-4,9(11)-diene-3,20-dione (7.0 g). After dissolution has occurred, THAM (tri-hydroxymethylaminomethane, 4.36 g) in water (16 ml) is added and the solution is allowed to stir at 20–25° for 18 hours. The mixture is then concentrated under reduced pressure at 350, and the resulting solids were azeotroped twice from absolute ethanol. Hot methanol (220 ml) is added to the crude solids, and after dissolution has occurred, an additional acetone (75 ml) is added. Crystallization is allowed to proceed at 20–25° for 18 hours. The resulting solids are filtered and washed well with methanol/acetone (2/1) followed by ether to give, after drying at 40° under reduced pressure the title compound, mp=177–179°; NMR($D_2O$) 6.0, 5.65, 5.63, 5.35, 4.70, 3.70, 2.65–1.25, 1.35, 1.10 and 0.80 δ.

Example 6
6α-Fluoro-177α,21-dihydroxy-16α-methylpregna-4,9(11)-diene-3,20-dione (II)

Methanol (20 ml) and sodium methoxide (25%, 0.2 ml) is added to 6α-fluoro-17α,21-dihydroxy-16α-methylpregna4,9(11)-diene-3,20-dione 21-acetate (U.S. Pat. No. 3,291,815, 1.0 g) in methanol. The reaction mixture is neutralized with acetic acid and concentrated to dryness under reduced pressure. The concentrate is distributed between water and chloroform. The organic layer is separated and washed twice with water and dried over anhydrous sodium sulfate. The crude solid is chromatographed over silica gel eluting with ethyl acetate/hexane (35/65). The appropriate fractions are pooled and concentrated to give the title compound, mp 206–207°.

Example 7
6α-Methyl-17α,21-dihydroxypregna-4,9(11)-diene-3,20-dione 21-acetate (II)

See, International Publication WO 86/00907 for patent application PCT/DE85/00249.

Example 8
6α-Fluoro-17α-hydroxy-16α-methylandrosta-4,9(11)-dien-3-one 17β-carboxylic acid methyl ester 17-butyrate Part A THF (26 ml) and periodic acid (0.677 g) in water (10 ml) is added to 611 mg (1.62 mmol) of 6α-fluoro-17,21-dihydroxy-16α-methylpregna-4,9(11)-diene-3,20-dione (EXAMPLE 6, 611 mg). The resulting solution is heated at reflux for 2 hours, then cooled to 25° and concentrated under reduced pressure to a volume of 5 ml. Water (15 ml) is added to the residue and the resulting mixture is extracted with ethyl acetate (2×25 ml). The ethyl acetate extracts are combined, dried over anhydrous sodium sulfate, filtered, and concentrated to dryness. The crude material is crystallized from acetone/hexane to give 6α-fluoro-17α-hydroxy-16α-methylandrosta-4,9(11)-dien-3-one 17β-carboxylic acid, mp 213.8–214°, MS calculated 363.1971, found 363.1962.

Part B

Acetic anhydride (0.5 ml) and triethylamine (0.3 ml) are added to 6α-fluoro-17α-hydroxy-16α-methylandrosta4,9(11)-dien-3-one 17β-carboxylic acid (Part A, 300 mg). The resulting mixture is stirred at 20≈25° until dissolution occurrs, and then stirred for an additional 40 min. The reaction solution is concentrated to dryness under reduced pressure, and the residue is dissolved in methanol and allowed to sit at 25° for 30 min. Evaporation of the methanol and final drying under high vacuum gives crude 6α-fluoro-17α-hydroxy-16α-methylandrosta-4,9(11)-dien-3-one 17β-carboxylic acid 17-acetate in quantitative yield, TLC $R_f$=0.05 (ethyl acetate/hexane, 35/65).

Part C

The crude 17-acetate (Part B) is dissolved in THF (8 ml) and then treated with freshly prepared diazomethane in ether until all of the starting material appeared to have reacted by TLC. The crude product is purified by chromatography over silica gel eluting with ethyl acetate/hexane (25/75). The appropriate fractions are pooled and concentrated to give 6α-fluoro-17α-hydroxy-16α-methylandrosta-4,9(11)-dien-3-one 17β-carboxylic acid methyl ester 17-acetate, TLC $R_f$=0.6 (ethyl acetate/hexane (35/65); MS calculated 419.2234, found 419.2212.

Following the general procedure of EXAMPLE 8 (Part B) and making non-critical variations but using butyric anhydride, 6α-fluoro-17α-hydroxy-16α-methylandrosta4,9(11)-dien-3-one 17β-carboxylic acid 17-butyrate, is obtained, TLC $R_f$=0.05 (ethyl acetate/hexane, 35/65); MS calculated 433.2390, found 433.2377.

Following the general procedure of EXAMPLE 8 (Part C) and making non-critical variations but starting with 6α-fluoro-17α-hydroxy-16α-methylandrosta-4,9(11)-dien-3-one 17β-carboxylic acid 17-butyrate, the title compound is obtained, TLC $R_f$=0.5 (ethyl acetate/hexane, 35/65); MS calculated 447.2547, found 447.2533.

Example 9
6α-Fluoro-17α,21-dihydroxy-16α-methylpregna-1,4-diene-3,20-dione 21-phosphate combined with 2-amino-2-(hydroxymethyl)-1,3-propanediol (1:2)

Following the general procedure of EXAMPLE 5 and making non-critical variations but starting with 6α-fluoro-17α,21-dihydroxy-16α-methylpregna-4,9(11)-diene-3,20-dione (PREPARATION 1), the title compound is obtained, mp 161.5–162.5°.

Example 10
21-Bromo-6α-fluoro-17α-hydroxy-16α-methylpregna-4,9(11)-diene-3,20-dione (I)

Mesyl chloride (255 μl) is added to 6α-fluoro-17α,21-dihydroxy-16α-methylpregna-4,9(11)-diene-3,20-dione (II, EXAMPLE 6, 1.12 g) in pyridine (15 ml) at 0°. The reaction is allowed to stir at 0° for 3 hours and gradually allowed to warm to 20–25° over a period of 2 hours. Water (2 ml of) is added and the mixture is concentrated to dryness. The residue is distributed between water and chloroform and the resulting organic solution washed with saturated bicarbonate (3×) followed by water washes (2×). The mixture is dried over sodium sulfate and concentrated to dryness to yield the crude 21 mesylate. Chromatography over silica gel using ethyl acetate/hexane (35/65) as eluent, collecting and concentrating the appropriate fractions gives a material with an $R_f$=0.3. Crystallization from acetone/hexane gives the 21-mesylate, mp 201.5=202°.

The 21-mesylate (80 mg) is dissolved in acetone (5 ml) and lithium bromide (17 mg) is added. The reaction mixture is allowed to stir at 20–25° until the reaction appeared complete by TLC (ethyl acetate/hexane, 35/65; $R_f$=0.75). The reaction mixture is concentrated to dryness and the resulting residue dissolved in chloroform and washed twice with water. The organic layer is separated and dried over anhydrous sodium sulfate. Filtration and concentration to dryness gives the title compound, mp gives decomposition; M/S (theory=439.1284) found=439.1274.

Example 11
17β-Carboxy-6α-fluoro-17α-hydroxy-16β-methylandrosta-4,9(11)-dien-3-one 17-butyrate The compound is made by methods well known to those skilled in the art.

Example 12
17β-Carboxy-9β,11β-epoxy-6α-fluoro-17α-hydroxy-16α-methylandrosta-1,4-dien-3-one 17α-butyrate 17β-methyl ester The compound is made by methods well known to those skilled in the art.

Example 13
21-Bromo-3α,17α-dihydroxy-5α-pregnan-20-one
See J. Org. Chem., 33,1695 (1968).

Example 14
17α,21-Dihydroxypregna-1,4,9(11)-triene-3,20-dione
See U.S. Pat. Nos. 4,704,358 and 4,771,042.

CHART A

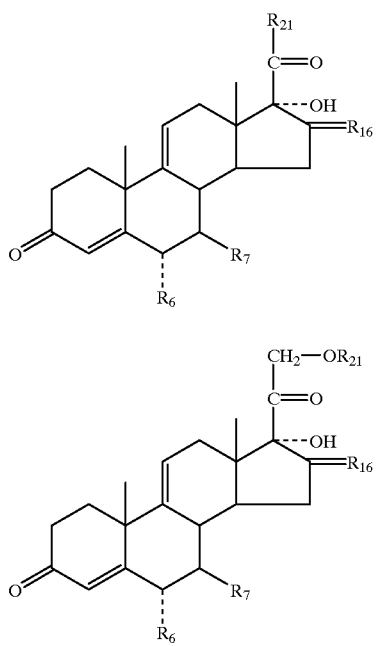

We claim:

1. A method of treating angiogenesis in a warm blooded mammal who is in need of such treatment which comprises administration of an angiogenic inhibiting amount of a $C_{21}$-oxygenated steriod of the formula:

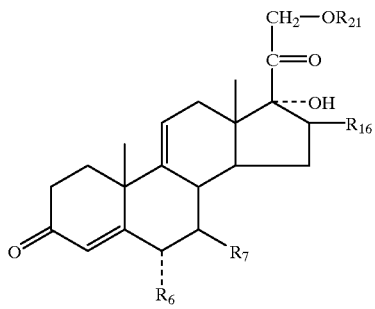

where $R_6$ is —H, —F or —$CH_3$;

$R_7$ is —H or —$CH_3$;

$R_{16}$ is H and $R_{21}$ is —CO—$R_{21\text{-}1}$ where $R_{21\text{-}1}$ is $C_1$–$C_{12}$ alkyl.

2. A method of treating angiogenesis according to claim 1 where the warm blooded mammal is a human.

3. A method of treating angiogenesis according to claim 1 where the $C_{21}$-oxygenated steroid (II) is selected from the group consisting of
   21-acetoxy-6α-methyl-17α-hydroxypregna-4,9(11)-diene-3,20-dione.

4. A method of treating angiogenesis according to claim 1 where the route of administration of the $C_{21}$-oxygenated steroid (II) is oral or parenteral.

5. A method of treating angiogenesis according to claim 1 where the dose of the $C_{21}$-oxygenated steroid (II) is from about 0.1 to about 100 mg/kg/day.

6. A method of treating angiogenesis according to claim 1 where the indication for treatment is selected from the group consisting of diabetes, arthritis, atherosclerosis, neovascularization of the eye, glaucoma, parasitic diseases, psoriasis, abnormal wound healing processes, hypertrophy following surgery, burns, injury, inhibition of hair growth, inhibition of ovulation and corpus luteum formation, inhibition of implantation and inhibition of embryo development in the uterus.

7. A method of treating angiogenesis in a warm blooded mammal who is in need of such treatment which comprises administration of an angiogenic inhibiting amount of the following compounds,
   6α-fluoro-17α,21-diacetoxy-16β-methylpregna-4,9(11)-diene-3,20-dione,
   21-bromo-3α,17α-dihydroxy-5β-pregnan-20-one,
   17β-carbomethoxy 6α-fluoro-17α-butanoyloxy-16α-methylandrosta-4,9(11)-dien-3-one,
   17β-carbomethoxy-9β,11β-epoxy-6α-fluoro-17α-butanoyloxy-16α-methylandrosta-1,4-dien-3-one,
   17β-carboxy-6α-fluoro-17α-butanoyloxy-16β-methylandrosta-4,9(11)-dien-3-one.

8. A method of treating angiogenesis according to claim 7 where the warm blooded mammal is a human.

9. A method of treating angiogenesis according to claim 7 where the route of administration is oral or parenteral.

10. A method of treating angiogenesis according to claim 7 where the dose is from about 0.1 to about 100 mg/kg/day.

11. A method of treating angiogenesis according to claim 7 where the indication for treatment is selected from the group consisting of diabetes, arthritis, atherosclerosis, neovascularization of the eye, glaucoma, parasitic diseases, psoriasis, abnormal wound healing processes, hypertrophy following surgery, burns, injury, inhibition of hair growth, inhibition of ovulation and corpus luteum formation, inhibition of implantation and inhibition of embryo development in the uterus.

* * * * *